United States Patent
Jaekel et al.

(10) Patent No.: US 12,006,277 B2
(45) Date of Patent: Jun. 11, 2024

(54) PROCESS FOR MAKING SOLID METHYLGLYCINE DIACETATE (MGDA) ALKALI METAL SALT, AND SOLID PARTICLES

(71) Applicant: BASF SE, Ludwigshafen am Rhein (DE)

(72) Inventors: Frank Jaekel, Ludwigshafen (DE); Michael Klemens Mueller, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 841 days.

(21) Appl. No.: 17/059,540

(22) PCT Filed: May 21, 2019

(86) PCT No.: PCT/EP2019/063042
§ 371 (c)(1),
(2) Date: Nov. 30, 2020

(87) PCT Pub. No.: WO2019/228849
PCT Pub. Date: Dec. 5, 2019

(65) Prior Publication Data
US 2021/0206712 A1    Jul. 8, 2021

(30) Foreign Application Priority Data
May 30, 2018   (EP) .................... 18175104

(51) Int. Cl.
*C07C 227/42* (2006.01)
*C07C 229/12* (2006.01)

(52) U.S. Cl.
CPC ........ *C07C 227/42* (2013.01); *C07B 2200/13* (2013.01); *C07C 229/12* (2013.01)

(58) Field of Classification Search
None
See application file for complete search history.

(56) References Cited

U.S. PATENT DOCUMENTS

| | | |
|---|---|---|
| 5,981,798 A | 11/1999 | Schoenherr et al. |
| 7,754,911 B2 | 7/2010 | Oftring et al. |
| 8,754,026 B2 | 6/2014 | Blei et al. |
| 2012/0283473 A1 | 11/2012 | Oftring et al. |
| 2020/0095189 A1 | 3/2020 | Kadam et al. |

FOREIGN PATENT DOCUMENTS

| | | |
|---|---|---|
| CN | 101171232 A | 4/2008 |
| CN | 103517894 A | 1/2014 |
| EP | 0845456 A2 | 6/1998 |
| WO | 2017102483 A1 | 6/2017 |

OTHER PUBLICATIONS

International Search Report and Written Opinion for corresponding PCT/EP2019/063042, dated Aug. 7, 2019, 6 pages.
International Preliminary Report on Patentability for International Patent Application No. PCT/EP2019/063042, dated Aug. 25, 2020, 5 pages.
Noriaki Hirayama, "Handbook for preparing crystal of organic compound", 2008, 28 pages.
European Search Report for EP Patent Application No. 18175104.1, dated Nov. 13, 2018, 3 pages.

*Primary Examiner* — Amy C Bonaparte
(74) *Attorney, Agent, or Firm* — Armstrong Teasdale LLP

(57) ABSTRACT

A process for making solid methylglycine diacetate (MGDA) alkali metal salt (a) includes:
(A) providing a 40 to 60% by weight aqueous solution of the MGDA salt having a temperature in the range of from 50 to 90° C.,
(B) adding solid salt (a),
(C) heating the resultant slurry until the salt (a) added in step (B) has dissolved at least partially,
(D) allowing salt (a) to crystallize, and
(E) removing crystalline salt (a) from the mother liquor.

6 Claims, No Drawings

PROCESS FOR MAKING SOLID METHYLGLYCINE DIACETATE (MGDA) ALKALI METAL SALT, AND SOLID PARTICLES

CROSS-REFERENCE TO RELATED APPLICATIONS

This application is a U.S. National Phase Application of International Patent Application No. PCT/EP2019/063042, filed May 21, 2019, which claims the benefit of priority to European Patent Application No. 18175104.1, filed May 23, 2018, the entire contents of which are hereby incorporated by reference herein.

The present invention relates to a process for making solid methylglycine diacetate (MGDA) alkali metal salt (a), said process comprising the steps of
- (A) providing a 40 to 60% by weight aqueous solution of said MGDA salt having a temperature in the range of from 50 to 90° C.,
- (B) adding solid salt (a),
- (C) heating the resultant slurry until the salt (a) added in step (B) has dissolved at least partially,
- (D) allowing salt (a) to crystallize,
- (E) removing crystalline salt (a) from the mother liquor.

In addition, the present invention relates to solid particles comprising a salt of MGDA.

Chelating agents such as methyl glycine diacetic acid (MGDA) and their respective alkali metal salts are useful sequestrants for alkaline earth metal ions such as $Ca^{2+}$ and $Mg^{2+}$. For that reason, they are recommended and used for various purposes such as laundry detergents and for automatic dishwashing (ADW) formulations, in particular for so-called phosphate-free laundry detergents and phosphate-free ADW formulations. For shipping such chelating agents, in most cases either solids such as powders or granules are being applied or aqueous solutions.

Depending on the type of product—liquid home care and fabric care products versus solid home care and fabric care products—and the manufacturing process of solid home care and fabric care products care product manufacturers may either prefer to handle solutions of aminocarboxylates or solid aminocarboxylates, for example joint spray drying or solid mixing. Powders and granules of aminocarboxylates may be shipped economically due to their high active ingredient content that goes along with low water content. Therefore, convenient processes for providing granules are still of great commercial interest.

However, granules and powders of MGDA and its respective alkali metal salts may be hygroscopic depending on the way they were obtained. Such hygroscopicity is undesired for various reasons. In powdery care formulations, the water may lead to lump formation that prevent the care formulation from flowing freely where desired. In addition, the water may create a medium wherein components of a formulation may react with and deactivate each other, for example bleaching agents and enzymes. Strongly hygroscopic mixtures may additionally show a tendency to yellowing when stored with percarbonate. Even in cases where the yellow colour does not prove a deterioration in quality consumers tend to avoid yellowing formulations.

In EP 0 845 846 A, a process to make crystalline salts of MGDA is disclosed. A water-containing super-cooled melt of MGDA is seeded with MGDA powder. The process has its shortcomings, though, because it is tedious to remove the crystals from the crystallization vessel.

It was the objective of the present invention to provide a process that leads to MGDA or its salts in solid form with low hygroscopicity. It was furthermore an objective to provide solids of MGDA or its salts with low hygroscopicity.

Accordingly, the process defined at the outset has been found, hereinafter also referred to as inventive process or process according to the present invention.

The inventive process is a process for making solid MGDA or its respective alkali metal salts, for example in form of a powder or of a granule. In the context of the present invention, the term "powder" refers to particulate materials that are solids at ambient temperature and that preferably have an average particle diameter in the range of from 100 nm to less than 0.1 mm, preferably 30 µm up to 75 µm. The average particle diameter of powders can be determined, e.g., by LASER diffraction methods, for example with a Malvern apparatus, and refers to the volume average.

The term "granule" in the context of the present invention refers to particulate materials that are solids at ambient temperature and that preferably have an average particle diameter (D50) in the range of from 0.1 mm to 2 mm, preferably 0.4 mm to 1.25 mm, even more preferably 400 µm to 1 mm. The average particle diameter of granules can be determined, e.g., by optical or preferably by sieving methods. Sieves employed may have a mesh in the range of from 60 to 3,000 µm.

The inventive process comprises of several steps, hereinafter in brief also referred to as step (A), step (B), step (C), step (D) and step (E), or (A), (B), (C), (D) or (E), respectively. Steps (A) to (E) will be outlined in more detail below.

As mentioned above, in step (A) an aqueous solution is provided. Aqueous solutions are defined herein as solutions with no solid particles detectable by visual inspection. Aqueous solutions may contain minor amounts of organic solvent that is or are miscible with water, for example ethanol, 1,2-propylenglycol, ethylene glycol, for example in a volume ration water:organic solvent 5:1 to 100:1. Preferably, however, aqueous solutions provided in step (A) do not contain detectable amounts of organic solvent.

Alkali metal salts of MGDA, hereinafter also referred to as component (a) or salt (a) or briefly (a), refers to methylglycine, partially or fully neutralized with alkali metal. Preferred examples of alkali metals are sodium and potassium and combinations of sodium and potassium.

In a preferred embodiment of the present invention, alkali metals of MGDA are selected from compounds according to general formula (I)

$$[CH_3-CH(COO)-N(CH_2-COO)_2]M_{3-x}H_x \qquad (I)$$

wherein

M is selected from alkali metal cations, same or different, for example cations of lithium, sodium, potassium, rubidium, cesium, and combinations of at least two of the foregoing. Preferred examples of alkali metal cations are sodium and potassium and combinations of sodium and potassium.

x in formula (I) is in the range of from zero to 1.0, preferred are zero to 0.5. In a particularly preferred embodiment, x is zero.

In one embodiment of the present invention, alkali metal salts of MGDA are selected from lithium salts, potassium salts and preferably sodium salts of MGDA. MGDA can be partially or preferably fully neutralized with the respective alkali. In a preferred embodiment, an average of from 2.7 to three COOH groups of MGDA is neutralized with alkali metal, preferably with sodium. In a particularly preferred embodiment, component (a) is the trisodium salt of MGDA.

MGDA and its respective alkali metal salts are selected from the racemic mixtures, the D-isomers and the L-isomers, and from mixtures of the D- and L-isomers other than the racemic mixtures. Preferably, component (a) is selected from the racemic mixture and from mixtures containing in the range of from 55 to 95 mole-% of the L-isomer, the balance being D-isomer. Particularly preferred are mixtures containing in the range of from 60 to 80 mole-% of the L-isomer, the balance being D-isomer. Other particularly preferred embodiments are racemic mixtures.

In any way, minor amounts of component (a) may bear a cation other than alkali metal. It is thus possible that minor amounts, such as 0.01 to 5 mol-% of total (a), bear alkali earth metal cations such as $Mg^{2+}$ or $Ca^{2+}$, or an $Fe^{2+}$ or $Fe^{3+}$ cation, or ammonium ($NH_4^+$).

In one embodiment of the present invention, component (a) may contain one or more impurities that may result from the synthesis of the MGDA. Examples of such impurities may be selected from propionic acid, lactic acid, alanine, nitrilotriacetic acid ("NTA"), iminodiacetic acid ("IDA"), carboxymethyl alanine ("CMA") and the like and their respective alkali metal salts. Such impurities are usually present in minor amounts. "Minor amounts" in this context refer to a total of 0.1 to 5% by weight, referring to component (a), preferably up to 2.5% by weight. In the context of the present invention, such minor amounts are neglected when determining the concentration of the aqueous solution provided in step (A).

The aqueous solution provided in step (A) has a concentration of component (a) In the range of from 35 to 60% by weight, preferably 40 to 50% by weight and even more preferably 40 to 45% by weight. The concentration may be determined, for example, by measuring the Fe(+III) binding capacity.

The aqueous solution provided in step (A) has a temperature in the range of from 50 to 90° C., preferably 60 to 80° C.

In one embodiment of the present invention, such aqueous solution according to step (A) has a pH value in the range of from 8 to 14, preferably from 9 to 13.5 and even more preferably at least 9.5. The pH value is determined at ambient temperature.

Solutions according to step (A) may be obtained by various methods. It is possible, e.g., to heat a given aqueous solution of component (a) to 50 to 90° C., or to dissolve component (a) in water under heating and, if applicable, removal of some of the water, for example by evaporation. In an alternative embodiment, it is possible to start the inventive process with a solution of component (a) that is stemming directly from the synthesis, in particular the saponification step, and to incompletely cool down such solution.

In step (B), solid salt (a) is added. Salt (a) may be added as crystals or as amorphous powder or as mixture of crystalline and amorphous product, crystals being preferred. Such solid salt (a) may be obtained, e.g., by spray drying or spray granulation of solutions of salt (a), or by any crystallization method, for example the method disclosed in WO 2012/150155 or EP 0 845 456 A.

In one embodiment of the present invention, the ratio of salt (a) in the solution provided in step (A) and salt (a) added in step (B) is in the range of from 0.5:1 to 2.4:1, preferably from 0.8:1 to 1.3:1.

Step (B) may be carried out by adding several aliquots of salt (a) or by adding all the salt (a) in one portion, the latter being preferred.

Step (B) may be performed without agitation or preferably under agitation, for example shaking or stirring, stirring being more preferred.

Step (B) leads to formation of a slurry.

In a preferred embodiment of the present invention, the slurry or solution formed in step (B) has a content of at least 48% by weight of salt (a).

In step (C), the slurry resulting from step (b) is heated until the salt (a) added in step (B) has dissolved at least partially, preferably fully. This heating includes raising the temperature.

In one embodiment of step (C), the temperature to which the slurry resulting from step (b) is heated is in the range of from 70° C. to the boiling point of the slurry, preferably 90° C. to the boiling point. E.g., heating to 70° C. implies that the temperature of the slurry at the end of step (b) is below 70° C., for example 45 to 65° C.

Preferably, the temperature of the resultant mixture at the end of step (C) is at least 15° C. higher than at the end of step (B), preferably in the range of from 20 to 75° C.

Step (C) may be performed under agitation, for example shaking or stirring, or without agitation. Stirring is preferred.

Step (C) is performed until the salt (a) added in step (B) has dissolved at least partially, preferably fully. The degree of dissolution of the salt (a) added in step (B) may be determined optically, for example visually or by light scattering.

In one embodiment of the present invention, the duration of step (B) is in the range of from 1 minute to 3 hours, preferably 30 to 3 hours.

By performing step (C), the salt (a) added in step (B) dissolves at least partially, preferably fully. A slurry or preferably a clear solution of salt (a) is formed.

In an optional step between steps (C) and (D), seed crystals of salt (a) are added, for example 0.01 to 3% by weight, the percentage referring to the content of (a).

In step (D), salt (a) is allowed to crystallize. Step (D) may be performed under agitation, for example shaking or stirring, or without stirring.

During step (D), crystallization may be enhanced by cooling of the solution of (a), or by allowing it to cool. By such cooling, the temperature may be decreased by 20 to 80° C. By cooling—or allowing to cool—the solution of (a), a slurry is obtained. It is noted that a solution provided in step (A) that has a temperature of about 90° C. may be cooled by up to 80° C. The final temperature should be at least zero ° C., preferably at least 10° C. and even more preferably at least 20° C. A possible upper temperature limit is 45° C.

Crystals of salt (a) are hereinafter also referred to as crystalline (a).

In step (E), said crystalline (a) is removed from the mother liquor. Such removal may be performed by filtration, for example with a belt filter or a strainer. The filter may have a pore diameter in the range of from 7 to 30 μm. Operations such as one or more washing steps and drying, for example vacuum drying, may be performed after filtration.

The inventive process also furnishes a mother liquor that may be "recycled", for example by adding solid alkali metal salt of MGDA and again performing the inventive process.

In a special embodiment, some crystalline (a) obtained by the inventive process may be recycled using them in step (B), optionally after milling them down to an average particle diameter of 100 to 750 μm.

The yield of crystalline (a) may be in the range of from 10 to 95%, preferably 60 to 95%, referring to dissolved (a).

Crystalline salts of MGDA are obtained by the inventive process. They exhibit a remarkably low hygroscopicity and a particularly good stability towards percarbonates such as sodium percarbonate, and they exhibit a great purity and thus actives content, and they are particularly well suited for the manufacture of cleaners, for example hard-surface cleaners and in particular of automatic dishwashing detergents.

The invention is further illustrated by working examples.

WORKING EXAMPLES

General Remarks:

The X-ray powder diffractometer measurements were carried out on a D8 Advance® diffractometer from Bruker AXS (Karlsruhe). In reflection with Cu-K α-radiation was measured with a variable diaphragm adjustment on the primary side and on the secondary side. The measurement range was 2° to 80° 2-theta, the step width 0.01° and the measurement time per angle step 3.6 seconds. Based on the software TOPAS from Bruker optics, the relative amounts of the two polymorphic forms of (a) were determined.

The ee values were measured by polarimetry.

With exception of ee values and of degrees of crystallinity, percentages in the context of the examples refer to percent by weight unless expressly indicated otherwise.

Normal pressure: 1013 mbar. The abbreviation rpm stands for "rounds per minute".

Average particle diameters are (D50) values and are determined by sieving methods unless expressly noted otherwise.

Component (a.1): MGDA-$Na_3$ (ee: 26%), provided as 40% by weight aqueous solution, pH: 13. Component (a.2): MGDA-$Na_3$ (racemic), provided as 40% by weight aqueous solution, pH: 13

Example 1

Step (A.1): in a 2 L four-necked round bottom flask equipped with overhead stirrer, temperature measuring device and cooler was charged with 420 ml of a 40% by weight solution of component (a.1), corresponding to 545 g of solution, and heated to 90° C.

Step (B.1): under stirring, 205 g granule of (a.1) corresponding to 180 g (a.1) were added to the solution in the flask.

Step (C.1): under continuous stirring, the resultant slurry was heated to 90° C. within 10 minutes under formation of a clear solution, and then cooled to 80° C. Then, an amount of 7 g of crystalline MGDA-$Na_3$ were added.

Step (D.1): The resultant slurry was cooled to 21° C. with an ice bath and then stirred at 21° C. for six hours. After a few minutes, crystallization of MGDA-$Na_3$ was observed.

Step (E.1): The resultant slurry was then filtered. The pressure was raised to 0.5 bar and then to 1 bar. The resulting filter cake was dried at room temperature and under vacuum (ca. 200 mbar) for a period of 24 hours in a laboratory oven. Crystalline solid particles (SP.1) were obtained.

Example 2

Step (A.2): in a 2 L four-necked round bottom flask equipped with overhead stirrer, temperature measuring device and cooler was charged with 420 ml of a 40% by weight solution of component (a.2), corresponding to 545 g of solution, and heated to 90° C.

Step (B.2): under stirring, 205 g granule of (a.1) corresponding to 180 g (a.1) were added to the solution in the flask.

Step (C.2): under continuous stirring, the solution was heated to 95° C. within 10 minutes under formation of a clear solution and then cooled to 80° C. Then, an amount of 7 g of crystalline MGDA-Na 3 were added.

Step (D.2): The resultant slurry was cooled to 21° C. with an ice bath and then stirred at 21° C. for six hours. After a few minutes, crystallization of MGDA-$Na_3$ was observed.

Step (E.2): The slurry was then filtered. The pressure was raised to 0.5 bar and then to 1 bar. The resulting filter cake was dried at room temperature and under vacuum (ca. 200 mbar) for a 40 period of 24 hours in a laboratory oven. Crystalline solid particles (SP.2) were obtained.

Example 3

Step (A.3): in a 2 L four-necked round bottom flask equipped with overhead stirrer, temperature measuring device and cooler was charged with 420 ml of a 40% by weight solution of component (a.1), corresponding to 545 g of solution, and heated to 70° C.

Step (B.3): under stirring, 205 g granule of (a.1) corresponding to 180 g of (a.1) were added to the solution in the flask.

Step (C.3): under continuous stirring, the suspension was heated to 70° C. within 10 minutes and maintained at this temperature for 180 min.

Step (D.3): The slurry was cooled to 21° C. with an ice bath and then stirred at 21° C. for six hours.

Step (E.3): The slurry was then filtered. The pressure was raised to 0.5 bar and then to 1 bar. The resulting filter cake was dried at room temperature and under vacuum (ca. 200 mbar) for a period of 24 hours in a laboratory oven. Crystalline solid particles (SP.3) were obtained.

The results are summarized in Table 2.

C-(SP.4): Solid MGDA-$Na_3$, spray granulated in accordance with EP 2 470 496 B1, example 1

TABLE 2

Powder XRD analysis of inventive solid particles and a comparison sample

| Sample | Form I [%] | Form II [%] | Crystallinity [%] |
|---|---|---|---|
| SP.1 | 2.2 | 97.8 | 87 |
| SP.2 | 4 | 96 | 94 |
| SP.3 | 100 | 0 | 100 |
| C-SP.4 | 96 | 4 | 74 |

Form I—monoclinic
Form II—orthorhombic

Moisture Uptake and Percarbonate Stability Tests

By storing samples of (SP.1), (SP.2) (SP.3), and C-(SP.4) for 7 days at 35° C. and a relative humidity of 70% the moisture uptake may be determined. The weight increase corresponds to the moisture uptake.

In order to measure the percarbonate stability, the samples are stored for 26 days at 35° C. and a relative humidity of 70%. Specifically, the samples were stored in 50 ml glass vials having a lid with a 0.5 mm hole. The change in color was followed my measuring elrepho brightness values. The higher the elrepho brightness value the darker the sample.

The invention claimed is:

1. A process for making a solid methylglycine diacetate (MGDA) alkali metal salt (a), said process comprising the steps of (A) providing a 40 to 60% by weight aqueous solution of said MGDA salt having a temperature in the range of from 50 to 90° C.,
(B) adding solid salt (a),
(C) heating the resultant slurry until the salt (a) added in step (B) has dissolved at least partially,
(D) allowing salt (a) to crystallize, and
(E) removing crystalline salt (a) from the mother liquor, wherein in step (C), the resultant slurry is heated until a clear solution is obtained, and wherein between steps (C) and (D), seed crystals of the salt (a) are added.

2. The process according to claim 1, wherein step (E) is carried out by filtration or centrifugation.

3. The process according to claim 1, wherein the salt (a) is selected from compounds according to general formula (I)

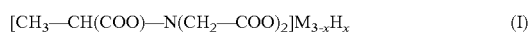  (I)

wherein:
M is selected from alkali metal cations, same or different, and
x in formula (I) is in the range of from zero to 1.0.

4. The process according to claim 1, wherein in step (D) the temperature is decreased by 20 to 90° C.

5. The process according to claim 1, wherein in the solid methylglycine diacetate (MGDA) alkali metal salt (a), the L-enantiomer is present by an enantiomeric excess in the range of from zero to 40%.

6. The process according to claim 1, wherein said process comprises an additional step of adding mother liquor from step (D) in whole or in part to an aqueous solution of methylglycine diacetate (MGDA) alkali metal salt (a) and adjusting its concentration to 35 to 60% by weight.

* * * * *